United States Patent
Shih et al.

(10) Patent No.: US 6,923,570 B2
(45) Date of Patent: Aug. 2, 2005

(54) THERMAL INTERFACE MATERIAL CHARACTERIZING SYSTEM

(75) Inventors: Chih C Shih, San Jose, CA (US); Cullen E. Bash, San Francisco, CA (US)

(73) Assignee: Hewlett-Packard Development Company, L.P., Houston, TX (US)

( * ) Notice: Subject to any disclaimer, the term of this patent is extended or adjusted under 35 U.S.C. 154(b) by 0 days.

(21) Appl. No.: 10/660,863

(22) Filed: Sep. 11, 2003

(65) Prior Publication Data

US 2005/0058178 A1 Mar. 17, 2005

(51) Int. Cl.⁷ .............................................. G01N 25/18
(52) U.S. Cl. ........................ 374/43; 374/44; 374/30
(58) Field of Search ........................... 374/43, 44, 30, 374/51, 46, 55, 56, 29

(56) References Cited

U.S. PATENT DOCUMENTS

| | | | | |
|---|---|---|---|---|
| 3,552,185 A | * | 1/1971 | Goode, Jr. et al. | 374/44 |
| 3,733,887 A | * | 5/1973 | Stanley et al. | 374/44 |
| 3,817,109 A | * | 6/1974 | Audet et al. | 374/44 |
| 4,630,938 A | * | 12/1986 | Piorkowska-Palczewska et al. | 374/44 |
| 4,840,495 A | * | 6/1989 | Bonnefoy | 374/43 |
| 5,258,929 A | * | 11/1993 | Tsuchida | 702/136 |
| 5,297,868 A | * | 3/1994 | Graebner | 374/44 |
| 5,940,784 A | * | 8/1999 | El-Husayni | 374/43 |
| 6,116,777 A | * | 9/2000 | Pause | 374/43 |
| 6,142,662 A | * | 11/2000 | Narh et al. | 374/44 |
| 6,183,128 B1 | * | 2/2001 | Beran et al. | 374/44 |
| 6,331,075 B1 | * | 12/2001 | Amer et al. | 374/44 |
| 6,748,350 B2 | * | 6/2004 | Rumer et al. | 374/43 |
| 2003/0072349 A1 | * | 4/2003 | Osone et al. | 374/43 |

FOREIGN PATENT DOCUMENTS

| | | | | | |
|---|---|---|---|---|---|
| DE | 3204028 A1 | * | 8/1983 | | G01N/25/18 |
| DE | 3638483 A1 | * | 5/1987 | | G01N/25/18 |
| FR | 2643717 A1 | * | 8/1990 | | G01N/25/18 |
| JP | 05149900 A | * | 6/1993 | | G01N/25/18 |

* cited by examiner

*Primary Examiner*—Gail Verbitsky
*Assistant Examiner*—Stanley J. Pruchnic, Jr.

(57) ABSTRACT

An automated test method characterizes the performance of commercially available thermal interface materials (TIM) for electronic cooling. Such automated internal test vehicle provides an independent study of various TIM's. A spectrum of materials are preferably tested using automated methods so the results are reported in a consistent way. Such reports simplify the comparison and selection of appropriate TIM material for various end-user applications. Such automated test method is observed to be faster and easier to use. It requires minimal operator intervention during the test.

21 Claims, 4 Drawing Sheets

THERMAL INTERFACE MATERIAL CHARACTERIZING SYSTEM

FIELD OF THE INVENTION

The present invention relates to material testing, and more specifically to a device and method for characterizing thermal interface materials while being subjected to automated pressure loads and thermal gradients.

BACKGROUND OF THE INVENTION

Modern high-speed, high performance systems require good thermal management. High temperatures can shorten component life and limit performance. So good system thermal performance must be included at the start of any new design. The power density of circuits has been increasing as the size of electronics continues to shrink.

Heatsinks have been a traditional way to help semiconductor devices to dissipate heat into the environment. Such heatsinks are typically made of finned aluminum and their bases are thermally coupled to the substrate of the semiconductor device. Very often, the heatsink must be electrically isolated from the substrate of the semiconductor device, so mica insulators and silicon gel are used between the heatsink and the device to pass the heat but block electrical current. A measure of how well the heat is coupled through is called the thermal resistance. It commonly is expressed as the thermal resistance between the active junction of a device and the ambient air. Forcing an airflow over the fins of an aluminum heatsink improves efficiency, especially between the heatsink itself and the ambient air.

Attaching a heatsink to heat-generating devices is one of the most inexpensive ways to manage heat build up. Minimizing the thermal resistance between heatsinks and the components to be cooled is a fruitful technology for efficient heat removal.

Many types of prior art thermal interface materials have been developed over the years to improve the heat transfer from heat-generating devices to their cooling systems and heatsinks. But manufacturers use a variety of ways to report material thermal resistance, such confuse end-users.

The industry standard ASTM D5470 test method is used to characterize a wide assortment of thermal interface materials ranging from dry pads to greases. A disadvantage of this conventional technique is it requires constant operator intervention to obtain a set of meaningful data. For example, the operator must place the specimen between the fixtures, manually apply load and heat, ensure the load is properly maintained during the unsteady-state, determine when the test reached steady-state, record temperatures at steady-state, and repeat all the steps for the next pressure level. The results are operator dependent, and often not repeatable.

Many suppliers have also either modified or incorrectly applied the standard method in such a way that it is difficult for the end-users to compare the data. Some common problems include using undersized samples and incorrect measurement of variables. If samples of TIM material are cut smaller than the cross sectional area of the test apparatus, they are likely to spread under compression and change the contact area. This is often not accounted for. Measured values like temperature and heat flow are often incorrectly applied and can lead to very large errors in reported data.

SUMMARY OF THE INVENTION

An object of the present invention is to provide a material test system for characterizing the performance of thermal interface materials.

Another object of the present invention is to provide a material test method for uniformly characterizing the performance of thermal interface materials.

Briefly, a thermal interface material test system embodiment of the present invention comprises a hot block and a cold block used to squeeze a test material between them. Different pressures and durations are used to fully characterize the thermal interface material's properties. A thermal gradient is developed across the test material and a variety of temperature measurements, pressure measurements, and time are logged. The thermal resistance of the test material is computed and made available to a user.

An advantage of the present invention is that a test system is provided for the uniform characterization of thermal interface materials.

Another advantage of the present invention is that an automated method is provided for the characterization of thermal interface materials.

These and other objects and advantages of the present invention will no doubt become obvious to those of ordinary skill in the art after having read the following detailed description of the preferred embodiment as illustrated in the drawing figures.

DETAILED DESCRIPTION OF THE EMBODIMENTS

Figure 1:
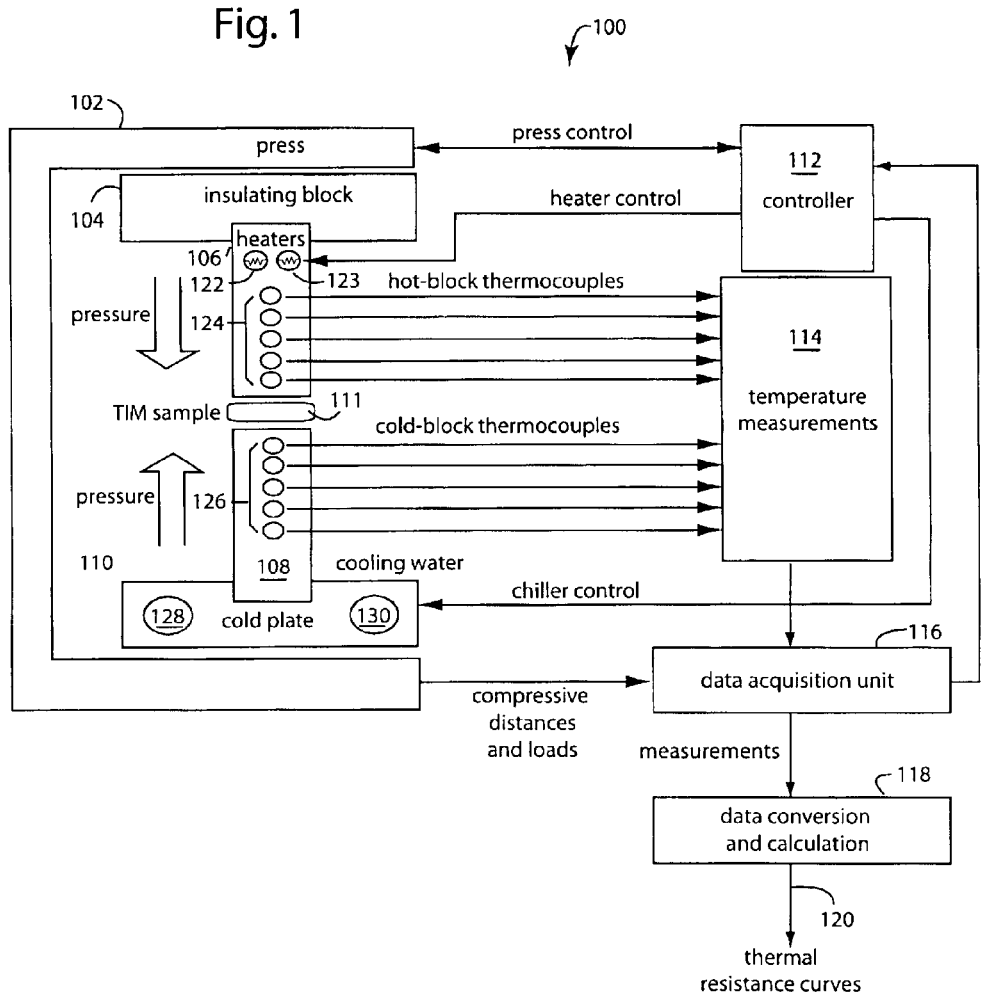
FIG. 1 is a schematic diagram of a thermal interface material test system embodiment of the present invention.

FIG. 1 illustrates a thermal interface material (TIM) test system embodiment of the present invention, and is referred to herein by the general reference numeral 100. The system 100 comprises a programmable press 102 in which are mounted a heat insulating block 104, a hot block 106, a cold block 108, and a cold plate 110. A "sample" TIM 111 is squeezed between the hot and cold blocks 106 and 108 during characterization. It is important that the pressure being applied remains constant even while TIM 111 expands and contracts over its programmed temperature excursions. An INSTRON 5566 can be used, as marketed by Instron Corporation, 100 Royall Street, Canton, Mass., 02021, USA. A gauge is useful for measuring the thickness of the TIM 111 at room temperature and at a test temperature.

A controller 112 manages how the programmable press 102 will operate during tests of the TIM, e.g., the pressures and durations applied. The controller 112 further adjusts the heat being applied and the cooling at the cold plate 110. A temperature measurement unit 114 collects thermocouple measurements and forwards these to a data acquisition unit 116. The measurements are all forwarded to a spreadsheet or other calculator 118 to produce thermal resistance curves 120. A least-squares fit of the temperature gradient is used for these measurements. Such can be used to characterize the material properties of TIM 111.

A computer is used for calculating a least-squares fit, with $R^2$ better than 0.99. Better than 99% of any variability in temperature will be related to differences in distance. Such is far more accurate than extrapolating temperatures using two thermocouples, e.g., as indicated in industry standard ASTM D5470. The accuracy or inaccuracy of thermocouple plays a bigger role in error when using only two thermocouples.

A pair of cartridge heaters 122 and 123 are set in the solid copper metal of hot block 106. A series of five thermocouples 124 are strategically placed to monitor heat flow to the TIM. Another set of five thermocouples 126 in the solid copper metal of cold block 108 are used to monitor heat flow away from the TIM into a cooling water 128 and 130.

A heat gradient curve is calculated from data collected from each set of thermocouples 124 and 126 to estimate the thermal resistance between and the temperatures that exist at each contacting face of the hot block 106 and cold block 108 with the TIM 111.

Figure 2:
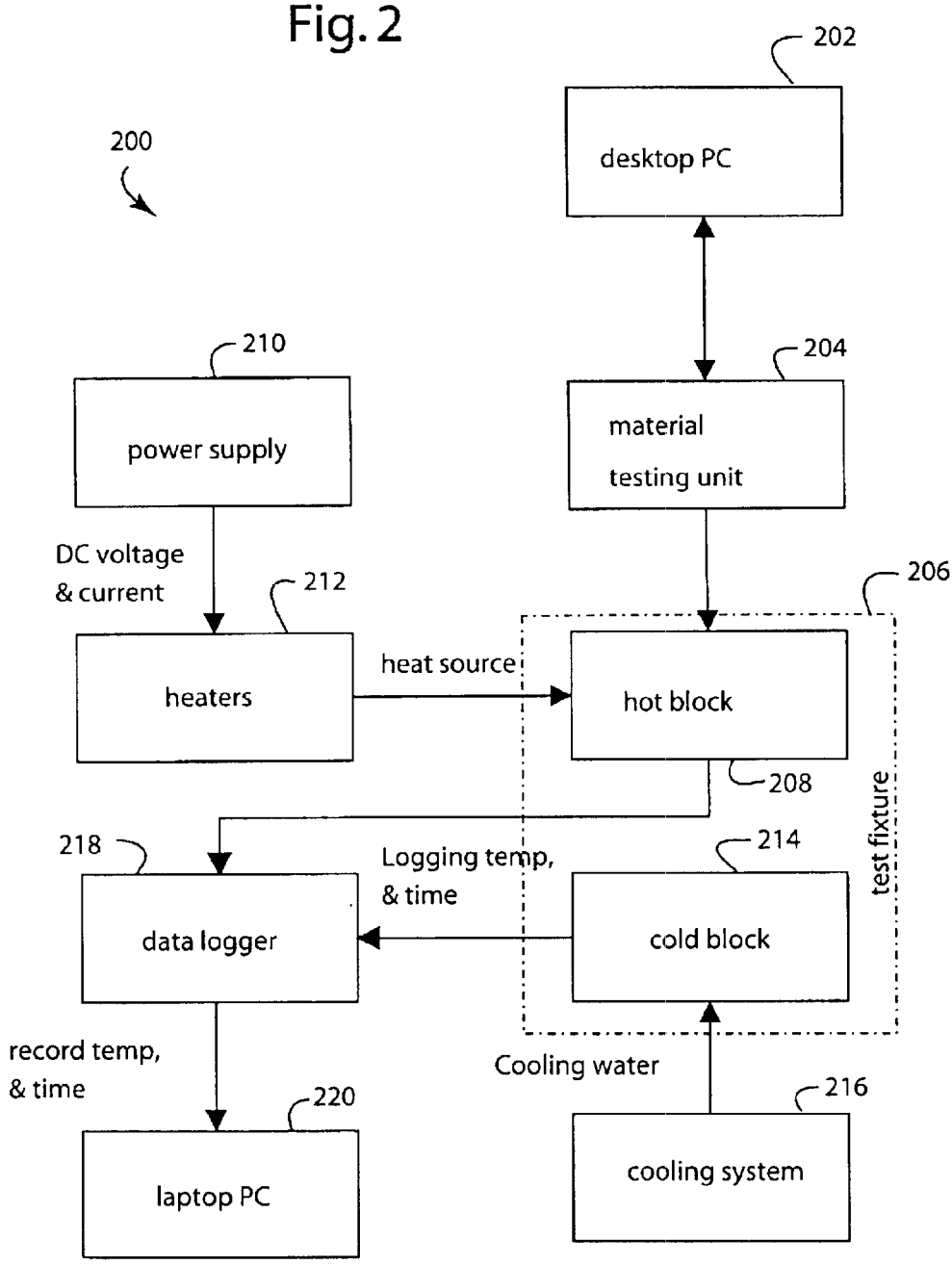
FIG. 2 is a functional block diagram of another thermal interface material test system embodiment of the present invention.

FIG. 2 represents another TIM testing system embodiment of the present invention, and is referred to herein by the general reference numeral 200. System 200 comprises a desktop personal computer (PC) 202 that interfaces with a material testing unit 204. A test fixture 206 responds with programmable pressures applied to a TIM sample placed between a hot block 208 and a cold block 209. A power supply 210 sends electrical power to a variable heater 212 attached to hot block 208. The heat generated is deliberately flowed through the TIM sample in order to gather measurements along the path of heat flow. A cooling system 216 chills the cold block 209 to generate a thermal gradient across the TIM sample. A data logger 218 collects temperature measurements and forwards them to a computer 220. The measurements and pressures applied to the TIM sample are used to characterize the TIM material.

Figure 3:
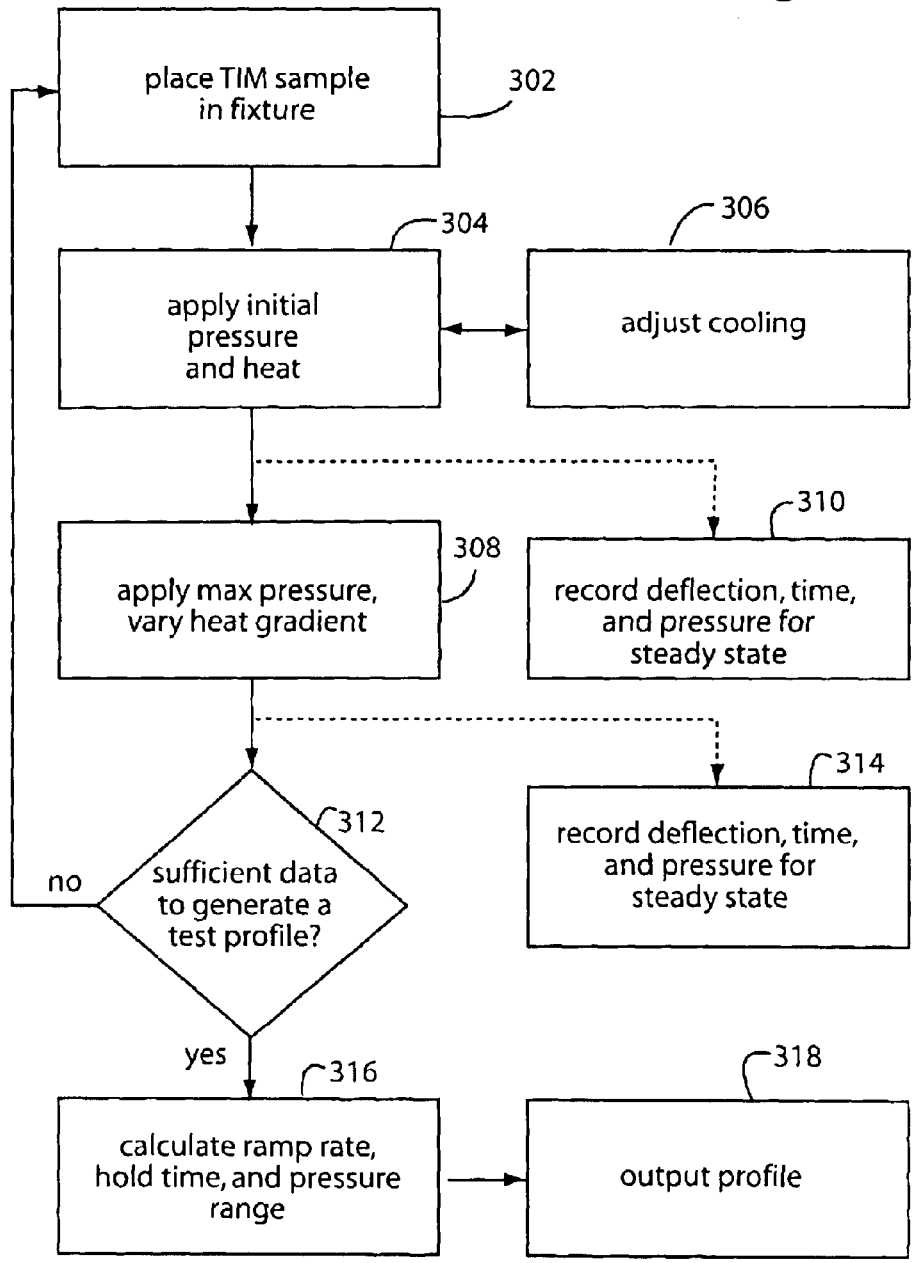
FIG. 3 is a flowchart diagram of a trial-run method embodiment of the present invention.

FIG. 3 illustrates a trial-run method embodiment of the present invention, and is referred to herein by the general reference numeral 300. Such trial run provides information about the initiate pressure, ramp rate, deflection allowed, and time required to reach steady-state conditions. The trial-run method 300 begins with a step 302 in which a TIM sample to be tested is placed between two contact blocks, e.g., a cold block and a hot block to generate a thermal gradient. Such blocks are included in a machine that can generate a variety of constant pressures for fixed durations on the TIM. A one inch square of TIM is used for convenience. An initial pressure and heat is applied in a step 304. Heaters and coolers are then adjusted in connection with the hot and cold blocks to generate useful temperature gradients across the TIM, as in a step 306. A maximum pressure is applied in a step 308. A data acquisition system is started in a step 310 to record temperatures at strategic points and times. A step 312 looks to see if sufficient data has been collected. If not, control returns to step 302. A step 314 continues data recording. A step 316 calculates ramp rates, hold times, and pressure ranges. A computer spreadsheet is pre-programmed to calculate thermal resistance curves and is loaded in real-time with the data collected. A final step 318 produces a thermal resistance curve for each particular TIM.

Figure 4:
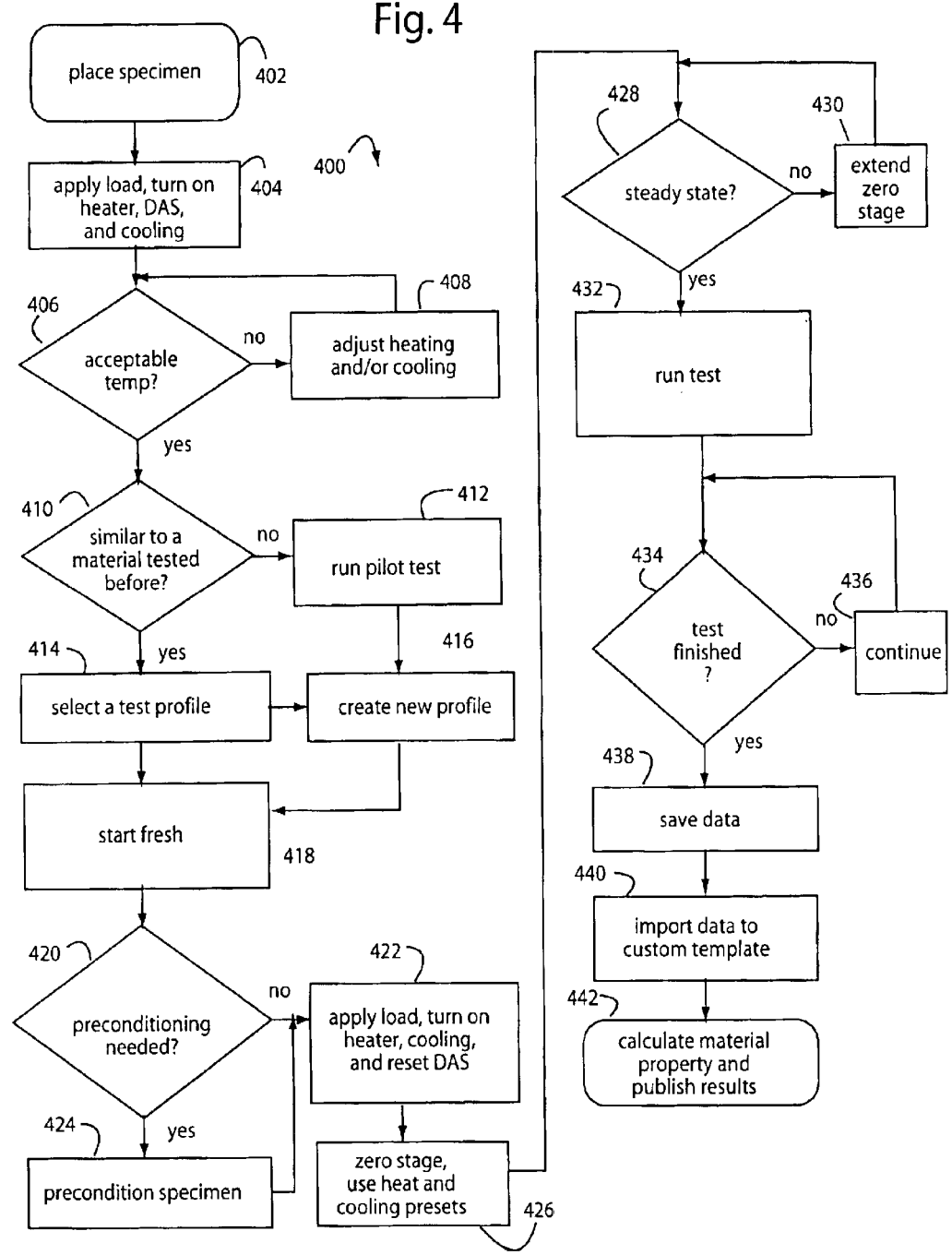
FIG. 4 is a flowchart diagram of a method embodiment of the present invention for testing the thermal properties of materials.

FIG. 4 illustrates a process method embodiment of the present invention, and is referred to herein by the general reference numeral 400. The process method 400 begins with a step 402 in which a TIM sample to be tested is placed in the fixture. A step 404 applies the pressure, heating, cooling, and starts the data logger. A step 406 looks to see if the temperature has reached a targeted value. If not, a step 408 adjusts the heating and cooling. A step 410 looks to see if a similar TIM material has been tested before. If not, a step 412 runs a pilot test like that of FIG. 3. A step 414 selects an appropriate profile from a library or database. A step 416 creates a new profile if needed. A step 418 starts the testing.

Pre-conditioning according to vendor instructions is used to optimize material properties before testing begins. Automating such preconditioning is useful to minimize any operator intervention needed.

A step 420 looks to see if preconditioning is needed. If not, a step 422 applies the profile of pressure, heat, cooling, duration, and starts data logging. A step 424 preconditions the TIM sample. A step 426 zeroes the fixture stage and uses heating and cooling presets. A step 428 looks for steady-state conditions. If not yet, a step 430 extends the zero stage. Otherwise, a step 432 runs the tests. A step 434 looks to see if the tests are finished. If not, a step 436 continues the testing. Otherwise, a step 438 saves the data logged. A step 440 imports that into a custom template. A step 442 calculates the TIM sample material properties and publishes the results. All the published results then allow a uniform way to compare different TIM materials under consideration.

Table I details three steps included in a spreadsheet calculation that was used in a prototype to estimate the thermal resistance of a TIM sample. The characterization of a TIM material includes pressurizing the material at several different levels and observing the thermal resistances at each of those pressure levels. TIM materials each behave differently in this regard, so trial runs are used to empirically determine the initial pressures, durations and increment of pressure, and rate of increase needed for formal TIM characterization. For example, the trial run of FIG. 3 is used before the formal process of FIG. 4. The "optimum" settings are then stored in a library.

In one prototype, an Instron computer was set up to capture time, pressures, and crosshead movement during the TIM test. The temperature profiles across TIM were captured by BENCHLINK data logger software loaded into a second computer, e.g., the laptop PC 220 (FIG. 2).

TABLE I

Step 1: Raw data conversion

The data acquisition unit recorded data in a laptop, and it was exported as a ".csv" file. The ".csv" file was imported into Excel "TIM_template". This raw data spread sheet provided the time stamps, and the temperatures of the corresponding channels.
Five thermocouple locations were included on the hot block, and five more
on the cold block. An eleventh thermocouple measured the cooling water temperature, and a twelfth measured the ambient temperature.
An Instron 5566 was used that reported the compression distance and load in ASCII-format. Such ASCII file was imported into a Microsoft EXCEL spreadsheet. The respective loads/distances were used by EXCEL to plot and output thermal resistance curves.

Step 2: Calculate interfacial temperatures

Each set of temperature measurements included five from hot block, and five from cold block. Measurements at steady-state were used as input to a linear Equation-for the corresponding distance/load. Such linear Equation-was used to calculate corresponding interfacial temperatures.

Step 3: Calculate and plot resistance curve

The corresponding slopes of the temperature gradients, wattage applied, and cross sectional area of the sample were input into the template to create the resistance curve.

A DC-power supply was used to power up an Omegalux CSH-101100 cartridge heater. Such is a high-density cartridge heater capable of generating 100-watts in limited space. This model was 0.25-inch in diameter and one-inch in length, with 300-series stainless steel sheaths.

An Agilent Technologies 34970A data acquisition unit made direct measurements of the thermocouples, thermistors, DC-voltage, AC-voltage, resistance, DC-current, AC-current, etc. It read up to 600-readings per second on a single channel, and scanned up to 250-channels per second. Such data logger can monitor twelve thermocouples or channels, e.g., five located at the hot block, five at the cold block, one at the cold plate, and one ambient. The interval scanning was set between 1–10 seconds, depending on the sample. An RS-232 interface was used to transfer time-stamped readings from the data logger to a laptop computer. The BENCHLINK data logger software was used to record the time, date, and a reading for each channel. Such data was imported into a spreadsheet template, so the temperature gradients across the copper blocks could be calculated.

The TIM test fixture used in the prototype comprised four parts, e.g., a hot copper block, a cold copper block, an insulating block, and an aluminum cold plate with copper tube. The hot copper block was 1.70 inches long, and the cross-sectional area of the testing face was one inch square. There were five 1/32 inch diameter and 0.55 inch deep holes in the block. The holes were 0.2 inch apart, and thermocouples were installed in each spot. Two quarter-inch diameter and one-inch deep holes were included the other end of the block for cartridge heaters on the non-testing face of the copper block. A polyetherimide insulating block was used to reduce heat losses. The cold copper block was similar in construction to the hot copper block, except no cartridge heaters were used there. The cold copper block was attached to an aluminum cold plate. Room temperature cooling water was run through the copper tubing to remove heat that made its way through the TIM and into the cold copper block.

TIM characterization included applying stepped amounts of pressure on the sample. The automation was mounted on one side of the test fixtures on a movable part of the material testing unit. Such unit was capable of providing compressive, crushing, forces exceeding 400-pounds. The system automatically measured the pressures applied to the material, the movement of the crosshead, movement between the specimen, and it attached a time-stamp. A computer connected to the unit was used to setup and capture data.

The data logger monitored temperature profiles across the custom fixtures. Depending on the sample, interval scanning was set to 1–10 seconds. An RS-232 serial interface was used to transfer time-stamped readings from the data logger to a second computer. The data logger software recorded time, date, and temperature readings for each sensor location. The data was imported into a custom spreadsheet. The temperature gradients across the fixture, and interfacial temperatures were calculated.

| | |
|---|---|
| A = | area (m²) |
| b = | intercept of the line |
| k = | thermal conductivity (W/(m · ° C.)) |
| m = | slope of the line |
| q = | heat transfer rate (W) |
| R = | thermal resistance (° C./W) |
| SSE = | the sum of square of the deviations of the y values about the least-squares line, if x is used to predict y |
| $SS_{yy}$ = | the sum of squares of the deviations of the observed y values about the best prediction of y values, if x is not used to predict y |
| T = | temperature (° C.) |
| x = | thickness (m) |

Conduction, convection and radiation are the three fundamental modes of heat transfer and govern heat removal from devices in the electronics industry. Conduction usually is the predominant mode of heat transfer inside a component, or between elements in contact. For one-dimensional, steady-state conductive heat transfer, the heat transfer rate per unit area is proportional to the temperature gradient, $$q = -kA \frac{\partial T}{\partial x}, \quad (1)$$

where, q is the heat transfer rate in one direction, T is the temperature, and the constants of proportionality are the thermal conductivity of the solid, k, and the cross-sectional area of the solid, A.

Equation-1 is Fourier's law of heat conduction. For heat transfer through a plane slab, integration of Equation-1 in the x direction yields, $$q = -\left(\frac{kA}{\Delta x}\right)(T_2 - T_1). \quad (2)$$

In Equation-2, q is the heat flow, the temperature differential across the slab is the driving force, while the thermal conductivity, cross-sectional area, and material thickness (x) combine to form the thermal resistance, R, of the solid. Using the electrical analogy, Fourier's Equation can be written, $$q = \frac{\Delta T}{R} \quad (3)$$

or $$R = \frac{\Delta T}{q} \quad (3a)$$

where, R, is ·x/kA, and is generally given in units of ° C./watt, and ·T=$T_1$–$T_2$ in ° C.

One of the ways in which to measure the thermal resistance of a piece of material is to sandwich the specimen between two isothermal conductive blocks and measure the temperature across the interface of the two blocks and the heat flow through the blocks and employ Equation-3a. Copper is generally a good choice because its high thermal conductivity relative to most specimens make it relatively easy to obtain an isothermal surface. The thermal resistance obtained by this method includes the interfacial resistance between the copper and TIM.

Thermal resistance is a function of material thickness and its conductivity. Most TIM materials are "compressible" and have particular "flow" properties. The application of higher pressures will reduce the effective thickness of the material and improve the thermal resistance.

The measured thermal resistance can be represented by:

$$R = \Sigma(R_1 + R_{TIM} + R_2) \quad (4)$$

where, $R_{TIM}$ is the thermal resistance of a bulk material, while $R_1$ and $R_2$ describe the interface resistance between the material under test and the conductive blocks.

The interfacial resistances are included in the measured value, resulting in an increase in the measured value over the "bulk resistance" of the TIM material. In real world applications, it is important to provide good interfacial contact, to reduce contact resistance. A material with poor rheology might form a poor interface, which adversely affects the heat flow. Therefore, it is necessary to include interfacial resistance in comparing the performance of the TIM materials. Also, it is advisable to use same type of material for the test fixtures, if possible, as in the actual application, to better represent the effect caused by the interfacial resistances.

The testing face of the hot copper block had a cross-sectional area of one inch square. There were five 1/32 inch diameter by 0.55 inch deep holes in the block. The holes were 0.2 inch apart, and thermocouples are inserted inside those holes. There were two quarter-inch diameter and one-inch deep holes at the other end of the block that housed the cartridge heaters. The non-testing face of the copper block with the cartridge heaters was fitted inside a polyetherimide insulating block to limit heat losses.

The construction of the cold block was similar to the hot block, the difference was there were no cartridge heaters inserted into the cold block. The cold copper block was fitted inside an aluminum cold plate. Cooling water at room temperature was passed through copper tubing in the aluminum cold plate to remove heat.

The automated test system can accommodate a wide variety of thermal interface materials. Each type of thermal interface material behaves differently, so trial runs are needed to determine initial conditions force, duration, increment of deflections/pressures, and rate of increase.

A trial run, as in FIG. 3, is used to determine initiate pressure, ramp rate, deflection allowed, and time required to reach steady-state. Steady-state is defined as the point when there are no further significant changes in temperature. A safety margin is added in the test profile to ensure the system reaches steady-state for each pre-determined pressure setting.

After a test profile has been established, a specimen is placed in the test fixture at a pre-set pressure, and temperatures are logged throughout the duration. Simple linear regression is used to determine the relationship between temperature and distance along each of the two copper blocks at steady-state. The least squares fit for a line is, $$y = mx + b \quad (4)$$

where, m is the slope and b is the intercept.
$R^2$, the correlation coefficient, is also calculated to determine the quality of fit.

$$R^2 = 1 - \frac{SSE}{SS_{yy}} \quad (5)$$

$$SSE = \Sigma(y_i - \bar{y})^2 \quad (5a)$$

$$SS_{yy} = \Sigma(y_i - \hat{y}_i)^2 \quad (5b)$$

where, SSE is the sum of the square of the deviations of the y values about the least-squares line, and $SS_{yy}$ is the sum of squares of the deviations of the observed y values about the best prediction of y values.

Data will be used when the $R^2$ value is ·0.99. That means, approximately 99% of the variability in temperature is related to the differences in distance.

The linear equations are used to estimate the interfacial temperatures at the hot and cold sides of the specimen.

The slope, m, of Equation-4, is the temperature gradient along the copper blocks. Since the thermal conductivity and cross sectional area of the copper blocks are known, the actual heat flow (q) through the specimen can be calculated using Equation-1, $$q = -kA \frac{\partial T}{\partial x}$$

Any heat loss to the environment has been accounted for and is thus more accurate than measuring the power supplied to the cartridge heaters.

The thermal resistance is calculated using Equation-3a $$R = \frac{\Delta T}{q}$$

where $\Delta T$ is the temperature difference across the specimen estimated with Equation-4.

A plot of thermal resistance with respect to pressure is made. Several TIM's are characterized. Their individual thermal resistances with respect to pressure are compared.

Embodiments of the present invention can be easily implemented by integrating as much off-the-shelf equipment as possible with a minimum of custom-built fixtures. Commercial screw-driven or hydraulic material testing units are combined with data loggers, power supplies and heaters, cooling systems, and personal computers, and custom fixtures. Finding the right component for a wide test window was challenging in the construction of prototypes.

Synchronizing the TIM testing units with the data loggers is important for a successful run. Such is made difficult by the fact theses are typically controlled by two independent software programs. A TIM test unit controls and records pressures, deflections, ramp rates, durations and time stamps. A data logger scans and records all temperatures reported by the thermocouples and their respective time stamps. Synchronizing the system enables an operator to export data with the same time stamp, making data processing much simpler.

The equipment set up should not be operator dependent, and no intervention should be required during a run. The continuous temperature scanning and display will determine the steady-state, not a randomly set time interval. The test profile predetermines the pressure/deflection for the entire run, no operator intervention in changing the setting. Such makes the process highly repeatable.

Test profiles are generated for every type of TIM to be tested. Each profile provides important information such as deflection rate, pressure ramp rate, duration, number of steps, and termination of the test. Using the same profile for similar material helps produce repeatable results.

The fixtures should minimize the measurement error induced by the tolerance of thermocouples. Proper positioning of the thermocouples along the blocks is key to the accurate measurement of the heat flowing through the TIM. A selection of $R^2=0.99$, or better, implies that approximately 99% of the variability in temperature is related to the differences in distance. This technique is used to reduce measurement errors associated with thermocouple inaccuracies.

Synchronizing the TIM testing unit and the data logger was important for a successful run because they were controlled by two individual software's. The TIM test unit controlled and recorded pressures, deflections, ramp rates, durations, and time stamps. The data logger scanned and recorded temperatures from the thermocouples and respective time stamps. Synchronizing the system enables the operator to export data with the same time stamp, making data processing much simpler.

The set up of equipment is not operator dependent. There should be no intervention required during a test run. Continuous temperature scanning and display are used to determine the steady-state, not a randomly set time interval. The test profile predetermines the pressure/deflection for the entire run, no operator intervention in changing the setting, making the process highly repeatable.

Embodiments of the present invention measure TIM pressure load and deflection at the same time. Correlations between load and deflection are therefore possible. Data from data logger and material tester can be imported into a custom EXCEL spreadsheet template to generates a TIM thermal resistance curve.

A materials testing method of the present invention places a thermal interface material (TIM) in a fixture between a hot and a cold copper block with parallel opposing faces. The TIM sample is squeezed between the opposing faces at a plurality of pressures and for a plurality of durations according to a test profile. A thermal gradient is generated across the TIM with a heater and cooler connected to the hot and cold copper blocks. The pressure applied to the TIM is adjusted to be constant even though the TIM expands and contracts with changes in its temperature. Temperature information is collected from the hot and cold copper blocks during the steps of squeezing and creating. A thermal-resistance-curve model of the TIM sample is built from data obtained in the step of collecting temperature information. The parallel opposing faces are automatically positioned to maintain parallelism between two contact surfaces so such precision is not operator dependent. No operator involvement is needed in test fixture assembling and offline measurements. The pressures applied between the parallel opposing faces is in the range of a few pounds to in excess of 400-pounds.

Cyclic tests are useful for special evaluations, and do not need to return to a particular starting point. For example, making all steps freely programmable and reversible is an advantage. A secondary heating block can be included to non-uniformly heat the TIM sample. Also, heating TIM samples from both sides during a pre-conditioning phase can minimize the wait time. Measurements of the TIM sample load and deflection are taken simultaneously. And it can be useful in characterization to correlate the TIM sample load and deflection.

Although the present invention has been described in terms of the presently preferred embodiments, it is to be understood that the disclosure is not to be interpreted as limiting. Various alterations and modifications will no doubt become apparent to those skilled in the art after having read the above disclosure. Accordingly, it is intended that the appended claims be interpreted as covering all alterations and modifications as fall within the true spirit and scope of the invention.

What is claimed is:

1. A test method, comprising:
squeezing a thermally conductive thermal interface material (TIM) sample at a plurality of different pressures at different times;
flowing heat through said TIM sample to create a gradient between a heat source and a cold sink at said plurality of different pressures;
measuring temperatures at a plurality of points along said thermal gradient at respective ones of said plurality of different pressures;
adjusting the pressure applied at each of said plurality of different pressures to maintain a constant pressure on the TIM sample even though said TIM sample expands and contracts with changes in its temperature; and
characterizing the thermal material properties of said TIM sample from calculations based on data obtained in the step of measuring following a time when the temperature measurements in the step of measuring should have reached a steady-state according to a previous trial run of said TIM sample.

2. The method of claim 1, further comprising:
delaying the step of characterizing until temperature measurements in the step of measuring have reached a steady-state.

3. The method of claim 1, further comprising:
first making a trial run of said TIM sample to determine a particular set of pressures to use in the step of squeezing.

4. The method of claim 1, further comprising:
first making a trial run of said TIM sample to determine a time delay needed for steady-state thermal conditions.

5. The method of claim 1, further comprising:
first making a trial run of said TIM sample to determine heating and cooling requirements needed to establish said thermal gradient.

6. The method of claim 1, further comprising:
computing a thermal resistance curve across intervening hot and cold blocks along said thermal gradient to extrapolate interface temperatures on opposite sides of said TIM sample; and
using said interface temperatures in a calculation of the thermal resistance of said TIM sample at each of said plurality of different pressures.

7. The method of claim 6, further comprising:
determining a relationship between temperature and distance along each of the hot and cold blocks at steady-state with simple linear regression.

8. A materials testing system, comprising:
a fixture for placing a thermally conductive thermal interface material (TIM) between a hot and a cold copper block;
a press for squeezing the TIM between the hot and cold copper blocks at a plurality of pressures and for a plurality of durations according to a test profile;
a heater and cooler connected to the hot and cold copper blocks for creating a thermal gradient across the TIM;
a compensating controller adjusting the pressure applied to the TIM to be constant even though said TIM sample expands and contracts with changes in its temperature;
a set of sensors for collecting temperature information from the hot and cold copper blocks during the steps of squeezing and creating; and
a computer for building a thermal-resistance-curve model of said TIM sample from data obtained in the step of collecting temperature information, wherein the computer is configured to build the thermal-resistance-curve model following a time when the temperature measurements in the step of collecting temperature information should have reached a steady-state according to a previous trial run of said TIM sample.

9. The system of claim 8, further comprising:
a gauge for measuring the thickness of said TIM sample at room temperature and at a test temperature.

10. The system of claim 8, further comprising:
a computer for calculating a net heat passing through said TIM sample to account for heat losses to the environment, and providing for a more accurate thermal resistance value to be estimated.

11. The system of claim 8, further comprising:
a plurality of thermocouples strategically disposed in the hot and cold blocks;

a computer for calculating a least-squares fit, with $R^2$ better than 0.99, that means better than 99% of the variability in temperature is related to the differences in distance.

12. The system of claim 8, further comprising:

a plurality of thermocouples strategically located and connected to provide data for a least-squares-fit for reducing a dependency on individual thermocouple accuracy.

13. A materials testing method, comprising:

placing a thermally conductive thermal interface material (TIM) in a fixture between a hot and a cold copper block with parallel opposing faces;

squeezing said TIM sample between said opposing faces at a plurality of pressures and for a plurality of durations according to a test profile;

creating a thermal gradient across the TIM with a heater and cooler connected to the hot and cold copper blocks;

adjusting the pressure applied to the TIM to be constant even though said TIM sample expands and contracts with changes in its temperature;

collecting temperature information from the hot and cold copper blocks during the steps of squeezing and creating; and building a thermal-resistance-curve model of said TIM sample from data obtained in the step of collecting temperature information following a time when the temperature measurements in the step of collecting temperature information should have reached a steady-state according to a previous trial run of said TIM sample.

14. The method of claim 13, further comprising:

automatically positioning said parallel opposing faces to maintain parallelism between two contact surfaces so the positioning of the parallel opposing faces is not operator dependent.

15. The method of claim 13, further comprising:

using no operator involvement in test fixture assembling and offline measurements.

16. The method of claim 13, further comprising:

applying pressure between said parallel opposing faces in the range of a few pounds to in excess of 400 pounds.

17. The method of claim 13, further comprising:

using cyclic tests for special evaluation without returning to a starting point.

18. The method of claim 13, further comprising:

non-uniformly heating said TIM sample with a secondary heating block.

19. The method of claim 13, further comprising:

heating TIM samples from both sides during a pre-conditioning phase to minimize wait time.

20. The method of claim 13, further comprising:

measuring TIM sample load and deflection simultaneously.

21. The method of claim 13, further comprising:

correlating TIM sample load and deflection.

\* \* \* \* \*

UNITED STATES PATENT AND TRADEMARK OFFICE
CERTIFICATE OF CORRECTION

PATENT NO. : 6,923,570 B2  Page 1 of 1
APPLICATION NO. : 10/660863
DATED : August 2, 2005
INVENTOR(S) : Chih C Shih et al.

It is certified that error appears in the above-identified patent and that said Letters Patent is hereby corrected as shown below:

In column 9, line 56, in Claim 1, before "gradient" insert -- thermal --.

In column 9, line 57, in Claim 1, before "said" insert -- each of --.

Signed and Sealed this

Twenty-eighth Day of July, 2009

JOHN DOLL
*Acting Director of the United States Patent and Trademark Office*